(12) United States Patent
Bordewick et al.

(10) Patent No.: US 6,854,465 B2
(45) Date of Patent: Feb. 15, 2005

(54) FACE MASK SUPPORT

(75) Inventors: Steven S. Bordewick, North Shoreview, MN (US); H. Stephen Quinn, Eau Claire, WI (US)

(73) Assignee: AEIOMed, Inc., Minneapolis, MN (US)

( * ) Notice: Subject to any disclaimer, the term of this patent is extended or adjusted under 35 U.S.C. 154(b) by 0 days.

(21) Appl. No.: 10/643,642

(22) Filed: Aug. 19, 2003

(65) Prior Publication Data

US 2004/0035427 A1 Feb. 26, 2004

Related U.S. Application Data

(60) Provisional application No. 60/404,685, filed on Aug. 20, 2002.

(51) Int. Cl.$^7$ ............................................. A62B 18/08
(52) U.S. Cl. .............................. 128/207.11; 128/207.13
(58) Field of Search ...................... 128/201.22, 201.23, 128/201.24, 205.25, 206.12, 206.18, 206.21, 206.27, 206.28, 207.11, 207.13, 207.17, DIG. 26; 2/410, 5, 6.1, 6.2, 6.6, 6.8, 417, 418, 421, 422, 424, 9, 171, 173, 202, 205, 206, 209, 908, 909, 912

(56) References Cited

U.S. PATENT DOCUMENTS

| 1,081,745 | A | * | 12/1913 | Johnston ................. 128/203.25 |
| 1,282,527 | A | * | 10/1918 | Bidonde ................. 128/201.11 |
| 1,632,449 | A | | 6/1927 | McKesson |
| 2,241,535 | A | | 5/1941 | Boothby et al. |
| 3,799,164 | A | | 3/1974 | Rollins |
| 4,151,843 | A | | 5/1979 | Brekke et al. |
| 4,593,688 | A | * | 6/1986 | Payton ................. 128/200.28 |
| 5,421,799 | A | * | 6/1995 | Rabin et al. ................. 601/71 |
| 5,538,000 | A | * | 7/1996 | Rudolph ................. 128/205.25 |
| 5,623,923 | A | * | 4/1997 | Bertheau et al. ........ 128/207.11 |
| 5,687,715 | A | | 11/1997 | Landis et al. |
| 6,119,693 | A | * | 9/2000 | Kwok et al. ............ 128/207.11 |
| 6,347,631 | B1 | | 2/2002 | Hansen et al. |
| 6,494,207 | B1 | | 12/2002 | Kwok |
| 6,505,623 | B1 | | 1/2003 | Hansen |
| 6,516,802 | B2 | | 2/2003 | Hansen et al. |
| 6,530,373 | B1 | * | 3/2003 | Patron et al. ........... 128/205.25 |
| 6,536,435 | B1 | * | 3/2003 | Fecteau et al. ......... 128/207.11 |
| 2002/0011248 | A1 | | 1/2002 | Hansen et al. |
| 2003/0051732 | A1 | | 3/2003 | Smith et al. |
| 2004/0025882 | A1 | * | 2/2004 | Madaus et al. ......... 128/206.27 |

* cited by examiner

Primary Examiner—Henry Bennett
Assistant Examiner—Teena Mitchell
(74) Attorney, Agent, or Firm—Kathleen R. Terry

(57) ABSTRACT

A face mask support for CPAP comprising a hemispheric cap with biasing means support at the medial line of the head. The circumferential edge of the cap extends from the high forehead to below the inion protrusion at the nape of the neck. A biasing means which is preferably of a length of spring steel is formed so as to extend from the biasing means support to form a loop around a face mask. The biasing means may be adjusted to accommodate facial configurations and to vary the pressure with which the face mask is apposed to the face. In an alternative embodiment, the support is open and is comprised of a circumferential band extending from the middle of the forehead to below the inion protrusion and a medial band extending along the medial line of the head and connecting to the circumferential band at the middle of the forehead and below the inion protrusion.

11 Claims, 4 Drawing Sheets

FACE MASK SUPPORT

CROSS REFERENCE TO RELATED APPLICATIONS

This invention claims the benefit under 35 U.S.C. § 119(e) of U.S. Provisional Application No. 60/404,685, filed Aug. 20, 2002.

FIELD OF THE INVENTION

This invention relates generally to a face mask support for providing pressurized gas to a patient. The mask support may be connected to a full face mask or a nasal mask. The pressurized gas may be ambient air, oxygen or a mixture thereof.

BACKGROUND OF THE INVENTION

As a person ages, airway patency may be reduced due to loss of muscle tone in the muscles of the throat which normally serve to prevent the tissues from impinging on the airway. This condition is more severe in patients who are obese, have naturally narrow airways or airways that may be partially blocked by tonsils, soft palate or uvula. The result can be snoring as the tissues vibrate as air is forced through the narrowed airway under heightened pressure. Snoring is disruptive to sleep; the snorer not only keeps companions awake but will himself awaken many times in the night. This sleep disturbance leads to a feeling of tiredness or exhaustion during the day and a decrease in mental and physical performance.

In about a third of snorers, the condition can be lethal. When narrowing of the airway proceeds to complete occlusion, the condition is termed sleep apnea. A faulty feedback loop between the brain and the respiratory system lets the airway completely collapse until the brain registers low oxygen levels and the patient jerks awake to resume breathing. These constant jump starts, which can happen as often as once a minute, send the heart rate on a roller coaster. In susceptible patients, high heart rates can bring on fatal arrhythmia or myocardial infarction.

Continuous positive airway pressure (CPAP) is a method in use for some time to alleviate the symptoms of snoring or sleep apnea by delivering air or gas under a pressure sufficient to mimic the effect of the natural waking tone of the throat muscles in holding the soft tissues around the airway from partially or totally occluding the airway passage. Patients other than those with airway problems can benefit from CPAP. These groups include patients with weakened respiratory muscles who cannot pull air into their lungs, such as those with post polio or amyotrophic lateral sclerosis disease, patients with traumatic nerve damage or adult respiratory distress. CPAP apparati are generally comprised of a blower for providing a stream of air or gas under pressure, a mask and tubing to connect the mask to the blower source. The mask can cover both the mouth and nose, the nose alone, or have plugs that insert only into the nares. Whatever the configuration, the mask must have, as a minimum, a means of sealing the mask to the face so that the blower gas does not escape, thereby reducing the pressure to the airway. Vents must be provided for exhaled gases. Preferably the vents are placed so as to avoid the eyes of the patient. A mask support is necessary to hold the mask and tubing in proper apposition.

Patient compliance is often a problem. Many of the masks currently available are uncomfortable, tend to be dislodged during sleep or disconnected from the blower source. If the mask is a full face mask covering both nose and mouth or a nasal mask covering only the nose, the peripheries of the mask will touch the bridge of the nose, the upper or lower lip and must seal around the malar region. Individual variations in the topography, especially of the malar region, make it necessary to hold the mask to the face with some pressure. It has been shown that a double seal, with a semirigid internal support and a flexible skirt can be inflated with air, forming a seal that more readily conforms to the malar region. The ideal mask support is usable with any variety of full face or nasal mask to accommodate individual needs and preferences.

The mask support must be capable of holding the mask firmly in position with as low a pressure as possible to avoid irritation of the face, especially the bridge of the nose. A popular design comprises a rigid band cantilevered over the medial line of the skull, with the blower source tubing arranged and secured along the band. (U.S. Pat. Nos. 1,081,745 and 6,347,631.) The only points at which the support applies pressure to the patient are at the occipital lobe and the mask.

The need remains for a face mask support that is comfortable, does not apply pressure to small or sensitive areas of the head and is not easily dislodged or disconnected from its blower source.

SUMMARY OF THE INVENTION

A mask support for continuous positive airway pressure comprising a flexible cap and a blower source operably attached to the cap, the blower source being operably attached to a mask. The blower source is preferably a blower unit with external coil-supported, smooth interior tubing connecting the blower to the mask. The lower circumferential edge of the cap surrounds the head from below the inion protrusion of the occipital bone to a point on the medial line of the head defined by a diameter through the head from the occipital lobe to the forehead.

The cap is approximately hemispheric and is made of light, flexible material. The circumferential edge is provided with a means for tightening. The means can be elastic inserts, buckles, draw strings or the like or the entire assembly may be constructed of an elastic material. The medial line from occipital lobe to forehead is reinforced with a flexible but firm band.

The open cap embodiment is comprised of a band defining the circumferential edge and a medial band passing over the approximate medial line of the head and attaching to the circumferential band at the forehead and below the inion protrusion of the occipital bone. The circumferential band is preferably provided with means for adjustment. The medial band may be bifurcated above its attachment to the back of the circumferential band. When the medial band is bifurcated, each arm is separately connected to the circumferential band, close to the medial line. The circumferential and medial bands may be formed from a single piece of material.

The medial band is fitted with a biasing means support that extends from just above the forehead attachment of the circumferential and medial bands back along the medial band to a point near the apex of the cranium. The biasing means support is approximately wedge shaped with the base curved to accommodate the curvature of the cranium and the top surface is at approximately a right angle to the vertical plane of the face and is comprised of a rigid or semi-rigid material so as to afford stable positioning for the biasing means. The biasing means support comprises at least one slot for the insertion of the ends of the biasing means.

The biasing means is comprised of spring steel, springs, or any metallic or plastic capable of transmitting force from one site to another, without fatigue. The biasing means is preferably a continuous length of spring steel formed into a loop and two equal length lateral arms, each end of which is insertible into the biasing means support, parallel to the top surface of the biasing means support and curved to an approximately 90 degree angle with the vertical plane of the face. The biasing means extends thus horizontally for a length sufficient to extend forward of the nose, and is at that point formed into a 90 degree curve so as to be parallel to the vertical plane of the face. The descending lateral arms form a loop that fits around the distal surface of the face mask. The mask support is adaptable to hold any full face or nasal mask in place. The descending lateral arms may also be separate length of spring steel, each independently inserted into biasing means and into the face mask at either its proximal or distal end.

Alternatively, the biasing means is a continuous length of spring steel with one end insertible into the biasing-means support, with the descending arm looped around the distal end of the mask and attached to the descending arm above the proximal end of the mask. The biasing means is fitted with an adjustment means which can be a ratchet or a friction hold. The tubing of the blower source passes between the lateral arms of the biasing means and attaches to the mask. The tubing may be secured to the top of the medial band at any point or at several points along the biasing means support.

The slots of the biasing means support are provided with means for adjusting the length of insertion of the ends of the arms of the biasing means, thereby adjusting the horizontal foreward length of the biasing means. The adjustment means may be a ratchet or friction hold. This adjustment accommodates both individual facial differences and the force to be applied to hold the face mask in position.

The circumferential band of the open cap is adjustable at each side of the head, the adjustment being by velcro, buckle, snap clamp or the like. Minor and quick adjustment may be provided by a cord with a slip clamp, which may be quickly pulled and released for minor adjustment and quick sizing. The medial band may likewise be provided with means for adjustment at the back of the head. When the medial band is bifurcated, each arm of the bifurcation may be provided with means for adjustment.

In the preferred embodiments, the mask support is made of soft, flexible material, while the biasing means support is a more rigid material and the biasing means is a very firm material. When the mask support is made of an elastic material, the means for adjustment may be eliminated. One skilled in the art can readily substitute materials to achieve the same or substantially the same support. Such supports are considered to be within the scope of the appended claims.

DETAILED DESCRIPTION OF THE INVENTION

For the purpose of defining this invention, "face mask" or "mask" is used to include any device for linking a positive pressure system (blower) to the airway of a patient. A face mask may be a mask that covers the full face, a mask that covers nose and mouth, a mask that covers only the nose or nasal plugs. A face mask support is any device that holds the face mask apposed to the face.

Figure 1:
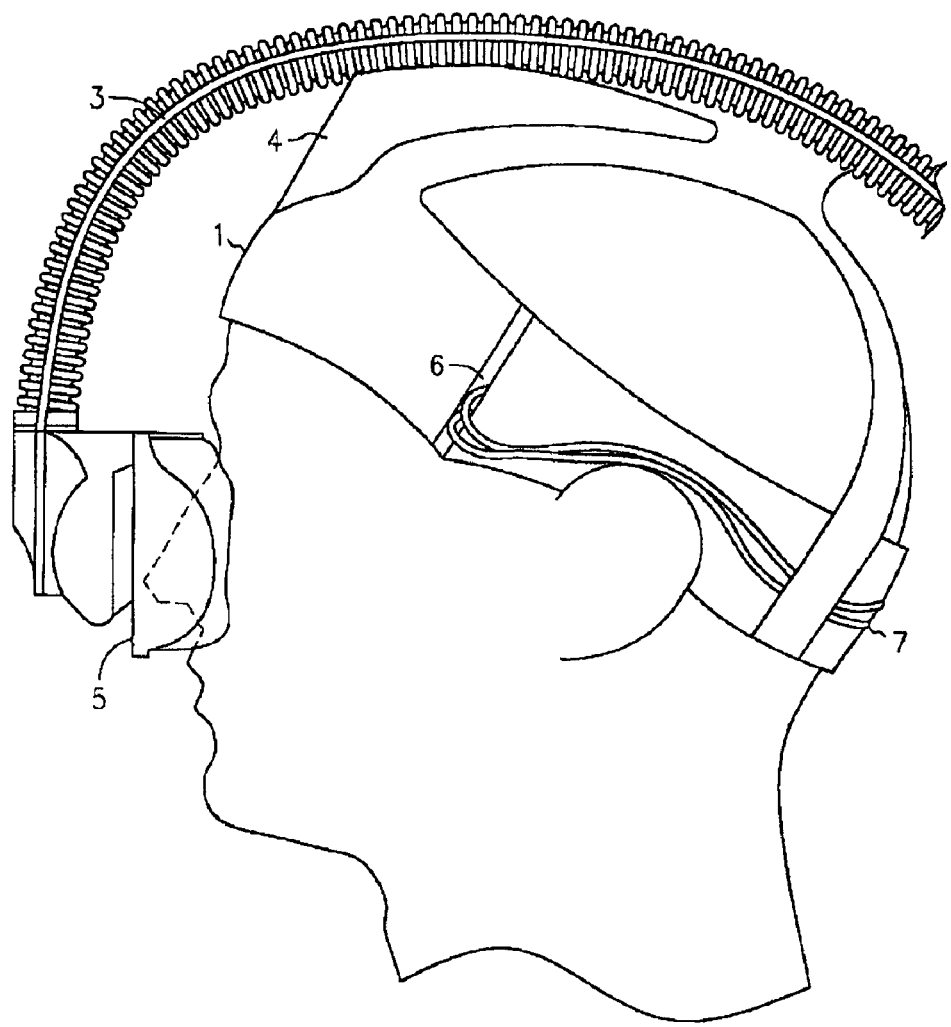
FIG. 1 shows a profile view of the open cap mask support of the invention.

Looking at FIG. 1, the circumference edge 1 of the open cap is seen to extend from the middle of the forehead, avoiding the sensitive eye and eyebrow regions, to below the inion protrusion of the occipital bone (the nape of the neck). The circumferential edge of either the open cap or the closed cap describes a hemisphere. This natural positioning gives stability to the mask support cap, in that the nape, where the spine joins the head, is the "low point" of the head, to which any encircling band will incline to rest. Thus, the circumferential band replaces both the forehead and occipital anchor points that are commonly found on similar devices. (See, e.g., U.S. Pat. No. 6,515,802.) The circumferential band is maintained on the head with loading that is applied independent of the loading of the face seal, unlike the supports in United States Patent Application U.S. 2002/0117177. The edge of the circumferential band 1 is joined at the forehead and the rear of the head to the medial band 2. Because the headband is sufficiently clamped, the medial band is sufficiently established such that it serves as a stable support for the biasing means support. With the medial band established on the medial line of the head, the biasing means is capable of creating a counter-clockwise moment needed to keep the mask apposed to the face, which translates the force into a clockwise moment of the mask loading force, tending to keep the mask on the face without leaking. The two arms of the biasing means 3 are inserted into the rigid or semi-rigid biasing means support 4 and are looped around the face mask 5. The circumferential band 1 is fitted with adjustment means 6 and quick-sizing cord 7.

Figure 2:
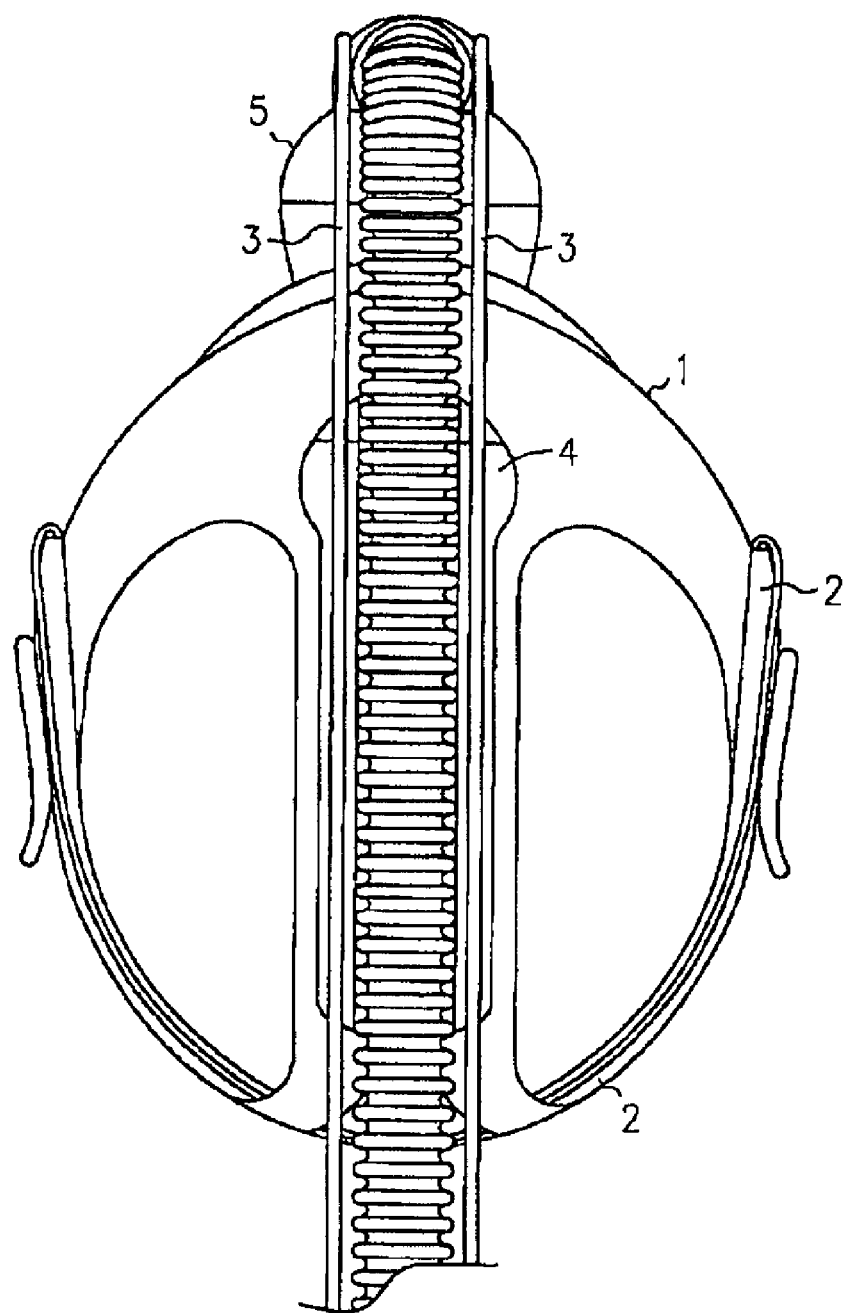
FIG. 2 shows a top view of the mask support of the invention.

Looking at FIG. 2, the circumferential band 1 is seen to extend from the middle of the forehead, avoiding the sensitive eye and eyebrow regions, to below the inion protrusion of the occipital bone (the nape of the neck). This natural positioning gives stability to the mask support cap, in that the nape, where the spine joins the head, is the "low point" of the head, to which any encircling band will incline to rest. The circumferential band 1 is joined at the forehead and the rear of the head to the medial band 2. The two arms of the biasing means 3 are inserted into the rigid or semi-rigid biasing means support 4 and are looped around the face mask 5.

Figure 3:
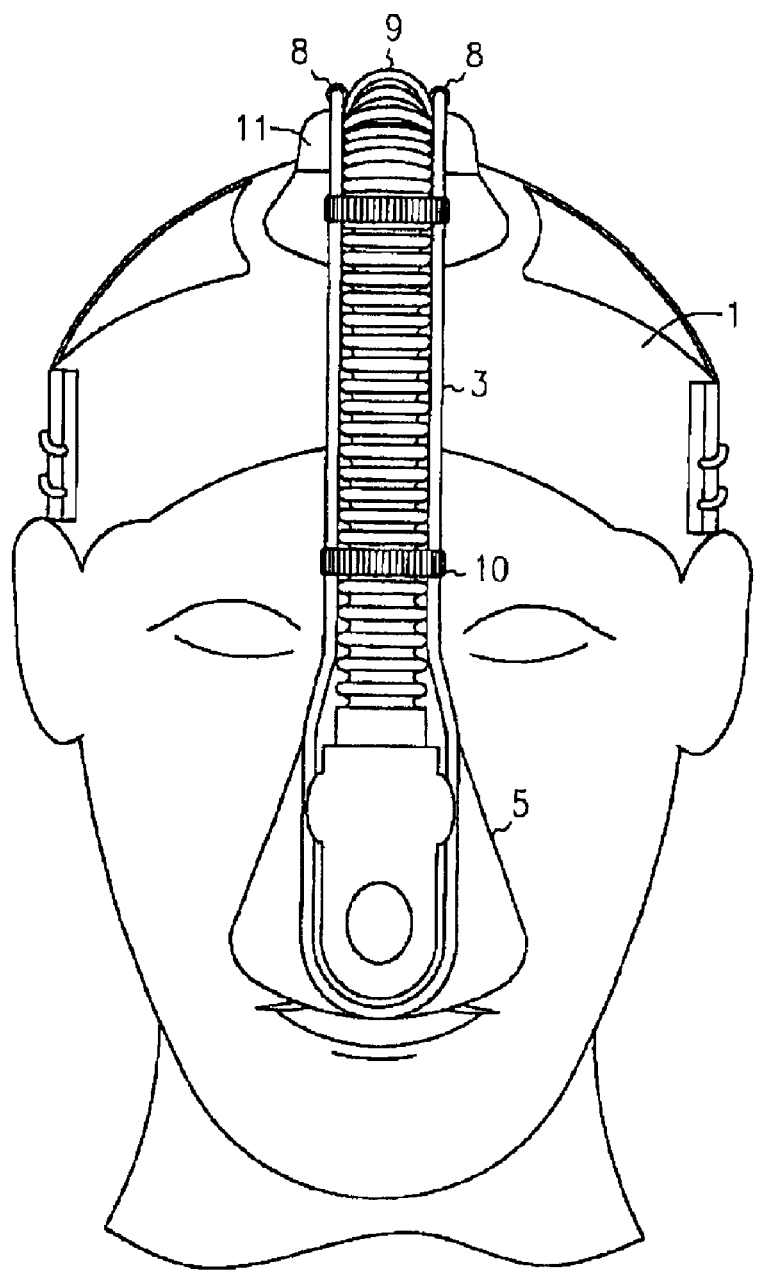
FIG. 3 shows a frontal view of the mask support of the invention.

Looking at FIG. 3, the frontal view of the mask support, the loop of the biasing means is shown to fit around the distal surface of the face mask 5. The adjustment 8 for the biasing means 3 may be a ratchet or a friction fitting. The air tube 9 passes through the groove formed by the loop of the biasing means. The air tube 9 may be secured to the biasing means at 10, the biasing means support at 11 or the medial band. Depending on the preference of the patient, the air tube may be free to swivel at any point, although most patients prefer to use the attchment 10 at the biasing means support to limit movement of the air tube.

Figure 4:
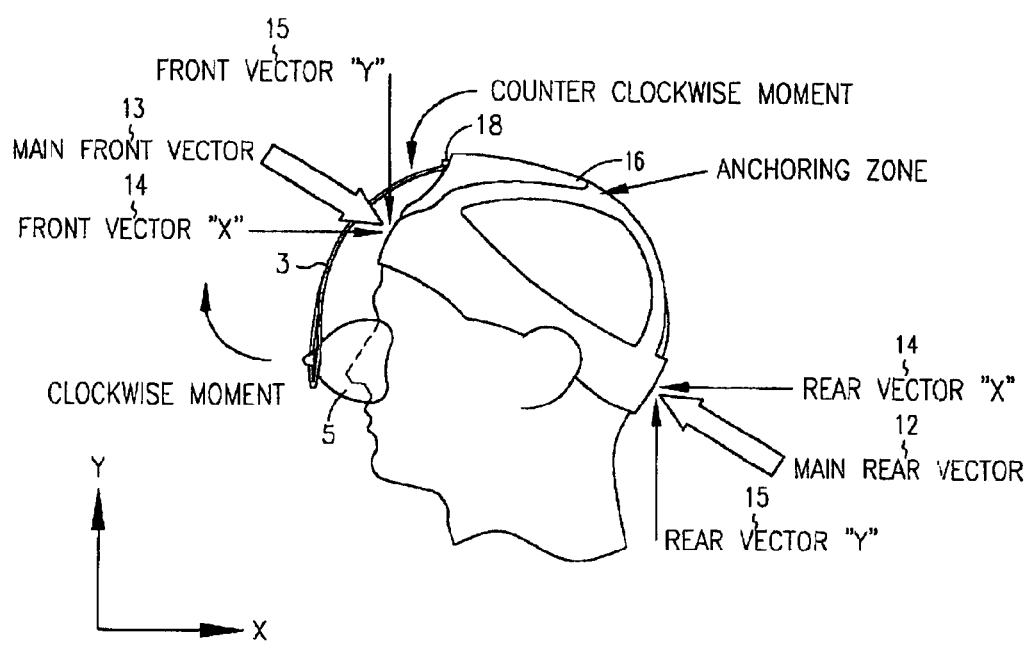
FIG. 4 shows the force vectors of the preferred embodiment of the mask support of the invention.

FIG. 4 shows the force distribution when the mask support, attached to a face mask 3 and blower system, is applied to a head, with the force necessary to hold the face mask apposed to the face. The force is transmitted from the top of the head to the face mask via the biasing means 3. It should be noted that the force will vary from patient to patient. The variables include:

higher or lower positive air pressure to hold the patient's airway open;

to provide adequate flow to a patient requiring breathing assistance;

a more restless patient who tends to dislodge the nosepiece;

to accommodate a patient's personal preference.

or an unusual topology of the patient's face. The biasing force may be increased or decreased by shortening or lengthening each arm of the biasing means at 8.

As noted, the loading of the circumferential band is applied independently of the loading for the face mask. The vectors created in tightening the band include the main rear vector 12 and the main front vector 13, which each occur normal to the surface of the head. The analysis of the resultant X 14 and Y 15 vectors show how the "clamping" of the head is accomplished. Noting the vectors X and Y, it can be seen that as the circumferential edge contacts the forehead at too high a position, clamping would fail because there would be no effective "undercut" for gripping and front vector X would be free to move the non rigid band back off of the head. Likewise, if the band contacts too high on the inion protrusion, rear vector Y would have no undercut to resist it and the flexible band would slip upward off of the head. Once the cap is sufficiently clamped by proper positioning of the hemispheric contour, the medial band is held on the medial line of the head and forms a stable anchor zone 16 for attachment of the biasing means support. The extensive stability of the anchoring zone established by the medial band allows for the use of a short length of rigid or semirigid material comprising the biasing means support. It should be noted that the biasing means support and the biasing means are the only components of the mask support that are not soft and flexible.

With this flexible but stable construction, the biasing means is capable of creating a counter-clockwise moment needed to keep the mask apposed to the face, which translates the force into a clockwise moment of the mask loading force, tending to keep the mask on the face without leaking and without the loading force being applied to a small anchor area.

In use, the patient adjusts the cap by means of the adjustment means 6 to a "loose comfort" and place the cap on his or her head, positioning it from the nape of the neck to the forehead. The patient then uses the quick-sizing cord 7 (on those embodiments which are provided with a quick-sizing means) to pull the cap snugly around the head. The medial bands are adjusted for proper fitting. The cap being fitted, the air tube from a blower is attached to a face mask so that the loop of the biasing means passes around the distal protuberance of the face mask. The ends of the biasing are fitted into the slot of the biasing means support and length l adjusted to accommodate variations in bias force required to hold the nose piece apposed to the patient's face. Once the original adjustments are made, the biasing means is left attached to the mask support. The mask support is totally soft and flexible except for the biasing means and the biasing means support, which rests on the patient's head from the upper forehead to the top of the cranium, which are areas less sensitive to pressure than the lower forehead and eye area. The result is a CPAP apparatus which is comfortable, stable and leads to increased patient compliance.

It may be understood that following the teachings of this patent application, those skilled in the art to which it pertains may readily make insubstantial changes, which changes are considered to be within the spirit and scope of this invention.

We claim:

1. A mask support for continuous positive airway pressure comprising:

a circumferential band adapted to encircle a head of a patient and to extend from a forehead of a patient to below an inion protrusion of an occipital bone of a patient;

a medial band operably connected to the circumferential band at a forehead and at an inion protrusion of an occipital bone and passing over the approximate medial line of a patient's head;

a biasing means support positioned on the medial band at a point from the apex of the skull to about the middle of a forehead and comprising at least two receiving slots;

a biasing means comprising a continuous length of rigid material fanned into a loop with two lateral arms of equal size, the ends of the arms being inserted into the receiving slots of the biasing means support and the lateral arms extending horizontally to a point forward to a nose of a patient and at that point curved downward at an approximately 90° angle to form descending arms the descending arms of a length to form a loop to encircle a face mask.

2. The mask support of claim 1 wherein the biasing means comprises spring steel.

3. The mask support of claim 1 wherein the receiving slots of the biasing means support comprise means for adjusting the horizontal length of the biasing means.

4. The mask support of claim 1 which comprises means for adjustment of the circumferential band.

5. The mask support of claim 1 which comprises means for adjustment of the medial band.

6. The mask support of claim 1 wherein the circumferential and medial bands are formed from a single piece of material.

7. The mask support of claim 1 wherein the medial band is bifurcated so as to form two arms and each arm of the medial band is connected to the circumferential band at each side of the medial line.

8. A mask support for continuous positive airway pressure comprising:

a circumferential band comprising an elastic material, said band adapted to encircle the head of a patient and to extend from a forehead of a patient to below an inion protrusion of an occipital bone;

a medial band comprising an elastic material operably connected to the circumferential band at a forehead of a patient and at an inion protrusion of an occipital bone of a patient and passing over the approximate medial line of a patient's head;

a biasing means support positioned on the medial band at a point from the apex of the skull to about the middle of a forehead and comprising two receiving slots;

a biasing means comprising a continuous length of rigid material formed into a loop with two lateral anus of equal size, the ends of the arms being inserted into the receiving slots of the biasing means support and the lateral arms extending horizontally to a point forward to a nose of a patient and at that point curved downward at an approximately 90° angle to form descending arms, the descending arms of a length to form a loop to encircle the distal end of a face mask.

9. A mask support for continuous positive airway pressure comprising:

a hemispheric cap, a circumferential edge of which is adapted to extend from a forehead of a patient to below an inion protrusion of an occipital bone;

a medial band operably connected to the circumferential edge of the cap at a forehead of a patient and at an inion protrusion of an occipital bone of a patient and passing over the approximate medial line of a patient's head;

a biasing means support positioned on the medial band at a point from the apex of a skull of a patient to about the middle of a forehead of a patient and comprising at least one receiving slot;

a biasing means comprising a continuous length of rigid material formed into a loop with two lateral arms of equal size, the ends of the arms being inserted into the at least one receiving slot of the biasing means support and the lateral arms extending horizontally and at that point forming an approximately 90° angle, to form descending arms of a length to encircle the distal end of a face mask.

10. The mask support of claims 1, 8 or 9 wherein the biasing means comprises at least one length of spring steel which connect individually or in combination with a face mask.

11. The mask support of claims 1, 6 or 8 wherein the biasing means comprises angular adjustments means for a face mask in the region approximately from where the descending arm or arms connect to or form a loop around the face mask.

* * * * *